(12) United States Patent
Conley (10) Patent No.: US 11,793,590 B2
(45) Date of Patent: Oct. 24, 2023

(54) INTRAMEDULLARY IMPLANT SCREW SELECTION DEVICE

(71) Applicant: Acumed LLC, Hillsboro, OR (US)

(72) Inventor: Brian Conley, Portland, OR (US)

(73) Assignee: Acumed LLC, Hillsboro, OR (US)

(*) Notice: Subject to any disclaimer, the term of this patent is extended or adjusted under 35 U.S.C. 154(b) by 205 days.

(21) Appl. No.: 17/198,972

(22) Filed: Mar. 11, 2021

(65) Prior Publication Data

US 2021/0282883 A1 Sep. 16, 2021

Related U.S. Application Data

(60) Provisional application No. 62/988,485, filed on Mar. 12, 2020.

(51) Int. Cl.
*A61B 90/00* (2016.01)
*A61B 17/72* (2006.01)
(Continued)

(52) U.S. Cl.
CPC .............. *A61B 90/06* (2016.02); *A61B 90/39* (2016.02); *A61B 17/7291* (2013.01);
(Continued)

(58) Field of Classification Search
CPC ... A61B 90/06; A61B 90/39; A61B 2090/061; A61B 2090/3966; A61B 17/7291; A61B 2017/564
See application file for complete search history.

(56) References Cited

U.S. PATENT DOCUMENTS 3,230,628 A * 1/1966 Hite .......................... G01B 3/04
D10/64
5,309,648 A * 5/1994 Allard ...................... G01B 3/30
33/783

(Continued)

FOREIGN PATENT DOCUMENTS

WO WO-2019046435 A1 * 3/2019 ............. A61B 17/62

OTHER PUBLICATIONS

"The intramedullary threaded nail for metacarpals designed by hand surgeons," INnate Surgical Technique Guide, 12000-0010 Rev F, 2019, 6 pages.
(Continued)

*Primary Examiner* — Kevin T Truong
*Assistant Examiner* — Diana Jones
(74) *Attorney, Agent, or Firm* — K&L Gates LLP (57) ABSTRACT

The present disclosure provides a medical device and method to determine proper implant screw sizing for inserting within the intramedullary canal of a patient's bone. The medical device includes a radiolucent base that includes radiopaque markings indicative of an implant screw. The markings therefore appear on a radiographic image taken of the provided medical device. The markings may include first diameter markings and length markings, and may also include second diameter markings. The first and second diameter markings may be indicative of a major and minor diameter of an implant screw, respectively. The markings may also include an indication of a type or model of implant screw. In some instances, the medical device may include multiple sets of markings. In such instances, each set of markings is indicative of a different implant screw.

20 Claims, 6 Drawing Sheets

(51) Int. Cl.
*A61B 17/86* (2006.01)
*A61B 17/56* (2006.01)

(52) U.S. Cl.
CPC ......... *A61B 17/86* (2013.01); *A61B 2017/564* (2013.01); *A61B 2090/061* (2016.02); *A61B 2090/3966* (2016.02)

(56) References Cited

U.S. PATENT DOCUMENTS

| 2004/0176770 | A1* | 9/2004 | Knopfle | A61B 17/86 |
| | | | | 33/549 |
| 2016/0081727 | A1* | 3/2016 | Munday | A61B 17/7291 |
| | | | | 606/62 |
| 2017/0007307 | A1* | 1/2017 | Cocaign | A61B 90/06 |
| 2018/0193106 | A1* | 7/2018 | McGinley | G01B 3/04 |
| 2019/0343569 | A1* | 11/2019 | Hedgeland | A61B 17/1725 |

OTHER PUBLICATIONS

"Reamer/Irrigator/Aspirator (RIA) Surgical Technique", DePuy Synthes, DSUS/TRM/0615/0627(1), Apr. 2017, 35 pages.
"Acumed Polarus 3 Solution Surgical Technique," Acumed LLC, Dec. 2016, 44 pages.

\* cited by examiner

INTRAMEDULLARY IMPLANT SCREW SELECTION DEVICE

PRIORITY CLAIM

The present application claims priority to and the benefit of U.S. Provisional Application 62/988,485, filed Mar. 12, 2020, the entirety of which is herein incorporated by reference.

BACKGROUND

Certain medical procedures require inserting a screw within a bone's intramedullary canal. For example, one method of treating a metacarpal fracture is to insert a screw within the metacarpal's intramedullary canal to hold the bone fragments together as the bone heals. To optimally fix the bone fragments and help promote proper healing, however, requires selecting a proper screw size for the corresponding patient. Selecting the proper screw size requires determining the intramedullary canal size that the screw will be inserted within, which requires capturing a radiographic image (e.g., an x-ray) of the affected region of the patient's body. One typical method of determining a proper screw size is to then measure the intramedullary canal size from the radiographic image and select the proper screw size based on the measured intramedullary canal size. This method, however, is time-consuming as it involves separate steps of capturing the radiographic image, measuring the intramedullary canal, and comparing the screw size options. It is also prone to error because the magnification of the radiographic image must be taken into account.

Another typical method of determining a proper screw size is a sizing device that is placed external to a patient's skin, and in line with the corresponding intramedullary canal, when capturing a radiographic image. The sizing device appears on the radiographic image overlaid on the image of the patient's bone, including the intramedullary canal. The radiographic image including the intramedullary canal and the sizing device may then help a medical professional determine a proper screw size. There are, however, various drawbacks to typical sizing devices of this nature.

One example sizing device is the INnate™ sizing guide instrument offered by ExsoMed™. The sizing guide instrument uses a metal rod that is placed external to a patient's skin over the affected bone, and is captured in a radiographic image. The metal rod includes multiple indicators to help a medical professional determine an implant length that should be used. The INnate™ sizing guide instrument, however, does not provide information to the medical professional regarding the proper implant diameter. For instance, only a single metal rod is imaged and thus the single metal rod's diameter is the only implant diameter appearing on the captured radiographic image. Moreover, the sizing guide instrument does not provide a medical professional with information regarding the major and minor diameters of a screw in relation to the intramedullary canal.

Another example sizing device is the implant sizer of the Acumed® Polarus® 3 system offered by Acumed®, the Applicant of the present application. The implant sizer is a metal strip with multiple implant length indicators. The Polarus® 3 implant sizer may be placed external to a patient's skin over the affected bone, and is captured in a radiographic image. The multiple implant length indicators may help a medical professional determine a proper humerus plate length. The Polarus® 3 implant sizer, however, does not provide information to the medical professional regarding the proper implant diameter. For instance, only a single metal strip is imaged and thus the single metal strip's diameter is the only implant diameter appearing on the captured radiographic image. Moreover, the implant sizer does not provide a medical professional with information regarding the major and minor diameters of a screw in relation to an intramedullary canal.

A third example sizing device is the radiographic depth gauge offered by DePuy Synthes™. The DePuy Synthes™ radiographic depth gauge is placed external to a patient's skin over the affected bone, and is captured in a radiographic image. The DePuy Synthes™ depth gauge includes multiple tabs indicating different diameters, some or all of which appear on the captured radiographic image. The multiple diameter tabs on the radiographic image help enable a medical professional to determine the patient's intramedullary canal diameter by determining the diameter tab that fills the imaged intramedullary canal. The DePuy Synthes™ depth gauge, however, does not provide information to the medical professional regarding a screw length. Additionally, the DePuy Synthes™ depth gauge does not provide a medical professional with information regarding the major and minor diameters of a screw in relation to the intramedullary canal.

Accordingly, a need exists for a screw sizing device that addresses the drawbacks of typical screw sizing devices discussed above.

SUMMARY

The present application relates generally to implant screw sizing. More specifically, the present application provides a new and innovative device for determining proper implant screw sizing in relation to a patient's intramedullary canal. In an example, a medical device includes a base component constructed of a radiolucent material and a set of markings on the base component. The set of markings are composed of a radiopaque material. The set of markings includes first diameter markings, second diameter markings, and multiple length markings. The first diameter markings are indicative of a first diameter of an implant screw. The second diameter markings are indicative of a second diameter of the implant screw, and are between the first diameter markings on the base component. The multiple length markings are indicative of a plurality of length options of the implant screw.

In another example, a medical device includes a base component constructed of a radiolucent material and multiple sets of markings on the base component. The multiple sets of markings are composed of a radiopaque material. Further, each set of markings is indicative of a specific implant screw. Each set of markings includes first diameter markings indicative of a first diameter of the specific implant screw and multiple length markings indicative of multiple length options of the specific implant screw.

In another example, a method includes positioning a medical device relative to a bone of a patient. The medical device may be one of the example medical devices described above. The area of the patient including the bone and the positioned medical device may then be exposed to radiation to generate a radiographic image. The generated radiographic image includes a reproduction of the set of markings on the medical device. Based on the radiographic image, a desired diameter and a desired length of the implant screw may be determined.

DETAILED DESCRIPTION

The present disclosure provides new and innovative devices and methods for determining proper implant screw sizing in relation to a patient's intramedullary canal. The presently disclosed device includes a radiolucent body material with radiopaque markings. When the device is radiographically imaged (e.g., x-rayed), the markings appear on the generated radiographic image (e.g., the x-ray), but the radiolucent body material does not appear on the image. The markings are indicative of various sizes of implant screws that may be utilized in a procedure. For example, the markings indicate a diameter of an implant screw. The markings also indicate multiple lengths that an implant screw may have. In some instances, the markings may indicate two or more separate diameters, either of a single implant screw or of different implant screws. For example, the first diameter markings may be indicative of an implant screw's major diameter (e.g., a distance between the outermost peaks of the threads) and the second diameter markings may be indicative of the implant screw's minor diameter (e.g., a distance between the valleys of the threads). In another example, the first diameter markings may be indicative of a first implant screw's diameter (e.g., major or minor) and the second diameter markings may be indicative of a second implant screw's diameter (e.g., major or minor).

Figure 1A:
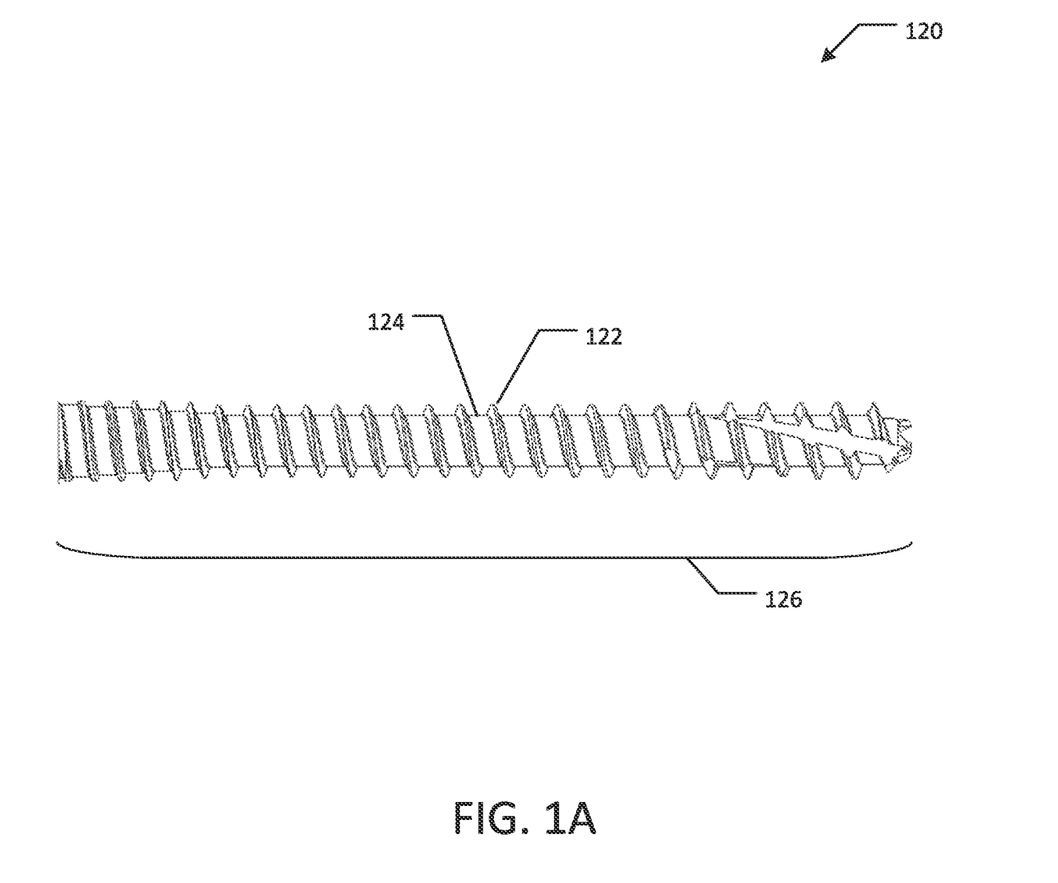
FIG. 1A illustrates an example implant screw that may be used in a medical procedure, according to an aspect of the present disclosure.

FIG. 1A illustrates an example implant screw 120 that some of the provided device's markings may be indicative of. The implant screw 120 has a major diameter 122 measured between the outermost peaks of its threads and a minor diameter 124 measured between the valleys of its threads. The implant screw 120 also has a length 126 measured from its two ends. In an example, the provided device may include markings that are indicative of different versions of the implant screw 120, with each version having the same major diameter 122 and minor diameter 124, but a different length 126.

In various instances, the provided device may include multiple sets of the above-described markings. For example, a first set may be indicative of an implant screw having a first diameter and a second set may be indicative of an implant screw having a second diameter that is greater or less than the first diameter. In such instances, all of the sets of markings on the device may appear on the generated radiographic image.

Accordingly, the presently disclosed device helps a medical professional to quickly and easily determine a proper implant screw diameter and length in a non-invasive manner either prior to the start of surgery or intraoperatively. Additionally, the presently disclosed device provides a medical professional with more information than typical implant screw sizing devices, such as those devices described in the Background section. For instance, the device may provide the medical professional with information on the major and minor diameters and the length of an implant screw in relation to a patient's intramedullary canal and/or may provide information on multiple implant screw sizes in relation to the intramedullary canal. Such additional information may help the medical professional better determine and/or more quickly determine the proper implant screw size for a patient. For instance, information on both the major and minor diameters of an implant screw may help a medical professional better understand how the implant screw will engage the patient's bone prior to the medical professional drilling or inserting the implant screw. In another instance, information on multiple implant screws having different diameters on the same radiographic image may help the medical professional better determine and/or more quickly determine a proper implant screw diameter size. Further advantages of the presently disclosed device and method will be apparent to one of skill in the art in light of the discussion in reference to the figures below.

Figure 1B:
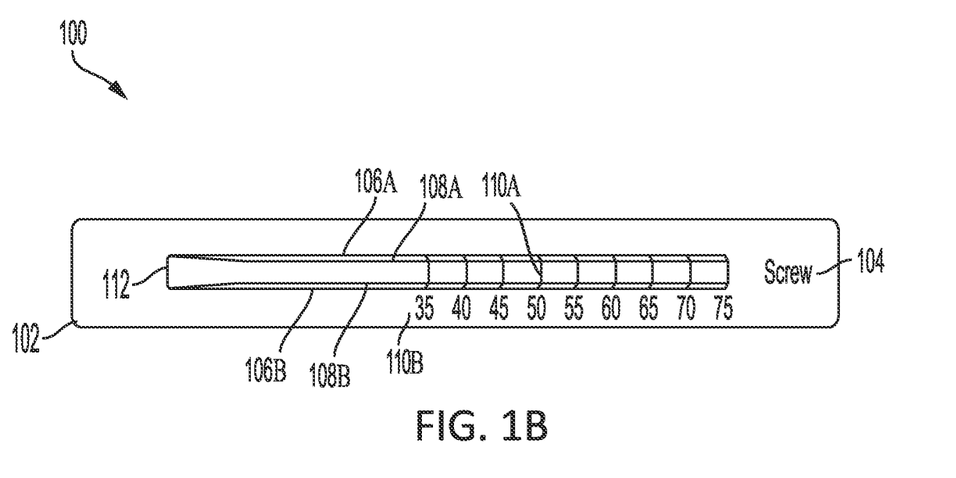
FIG. 1B illustrates an example medical device, according to an aspect of the present disclosure.

FIG. 1B illustrates an example medical device 100, according to an aspect of the present disclosure. The example medical device 100 includes a body 102. The body 102 includes a radiolucent material such that x-rays pass through the body 102. When the medical device 100 is radiographically imaged, the body 102 therefore fails to appear on the generated radiographic image. For example, the body 102 may be constructed of Polyether ether ketone (PEEK), acetal, ABS, nylon, carbon fiber polycarbonate, or other suitable materials.

The medical device 100 also includes a set of markings on the body 102. The set of markings include a radiopaque material that prevents x-rays from passing through the markings. When the medical device 100 is radiographically imaged, the markings therefore appear on the generated radiographic image. For example, the set of markings may be composed of barium sulfate, bismuth, tungsten, stainless steel, titanium, cobalt chrome, radiopaque inks, or other suitable materials. The set of markings are indicative of information pertaining to an implant screw. For example, the set of markings may include first diameter markings 106A, 106B indicative of a first diameter of an implant screw. In at least some examples, the set of markings may also include second diameter markings 108A, 108B indicative of a second diameter of an implant screw. In this example, the second diameter markings 108A, 108B are between the first diameter markings 106A, 106B. The first diameter markings 106A, 106B may be indicative of a major diameter of a threaded implant screw and the second diameter markings 108A, 108B may be indicative of a minor diameter of the threaded implant screw, in various aspects.

In such aspects, including both the major and minor diameters of a threaded implant screw on the medical device 100 may help a medical professional better understand, when analyzing a radiographic image including the markings, how the implant screw will engage the patient's bone. For instance, the medical professional is able to analyze the positioning of the implant screw's threads relative to the wall of the intramedullary canal to determine a portion of the threads that will engage the patient's bone. Providing the medical professional with this information prior to drilling or inserting the implant screw into the patient may help the medical professional select a proper-sized implant screw. Selecting the proper-sized implant screw may help the medical professional best perform medical procedures involving the implant screw.

In other aspects, the first diameter markings 106A, 106B may be indicative of a diameter (e.g., major diameter) of a first implant screw and the second diameter markings 108A, 108B may be indicative of a diameter (e.g., major diameter) of a second implant screw. In such other aspects, the set of markings may include additional diameter markings, such as major and minor diameter markings for the first implant screw and major and minor diameter markings for the second implant screw. The markings corresponding to the first implant screw may be distinguished from the markings corresponding to the second implant screw. For example, the first implant screw markings may be solid lines while the second implant screw markings may be dashed lines.

The set of markings may also include a screw indicator 104. In some aspects, the screw indicator 104 may indicate a diameter of the implant screw, such as the major diameter and/or the minor diameter. In other aspects, the screw indicator 104 may indicate a type or model of implant screw. For example, the model of implant screw may be a 5.5 Acutrak® 2, a 4.7 Acutrak® 2, or a standard Acutrak® 2 implant screw offered by Acumed®, the Applicant of the present application. Other types of implant screws may include headed cannulated screws or metacarpal screws. Including the screw indicator 104 on the medical device 100 enables a medical professional, when analyzing a radiographic image including the set of markings, to quickly understand which set of markings correspond to which implant screw. It also eliminates the need for the medical professional to have to consult materials or information outside of the radiographic image itself. Accordingly, these advantages decrease procedure time and decrease a risk of error.

Figure 1C:
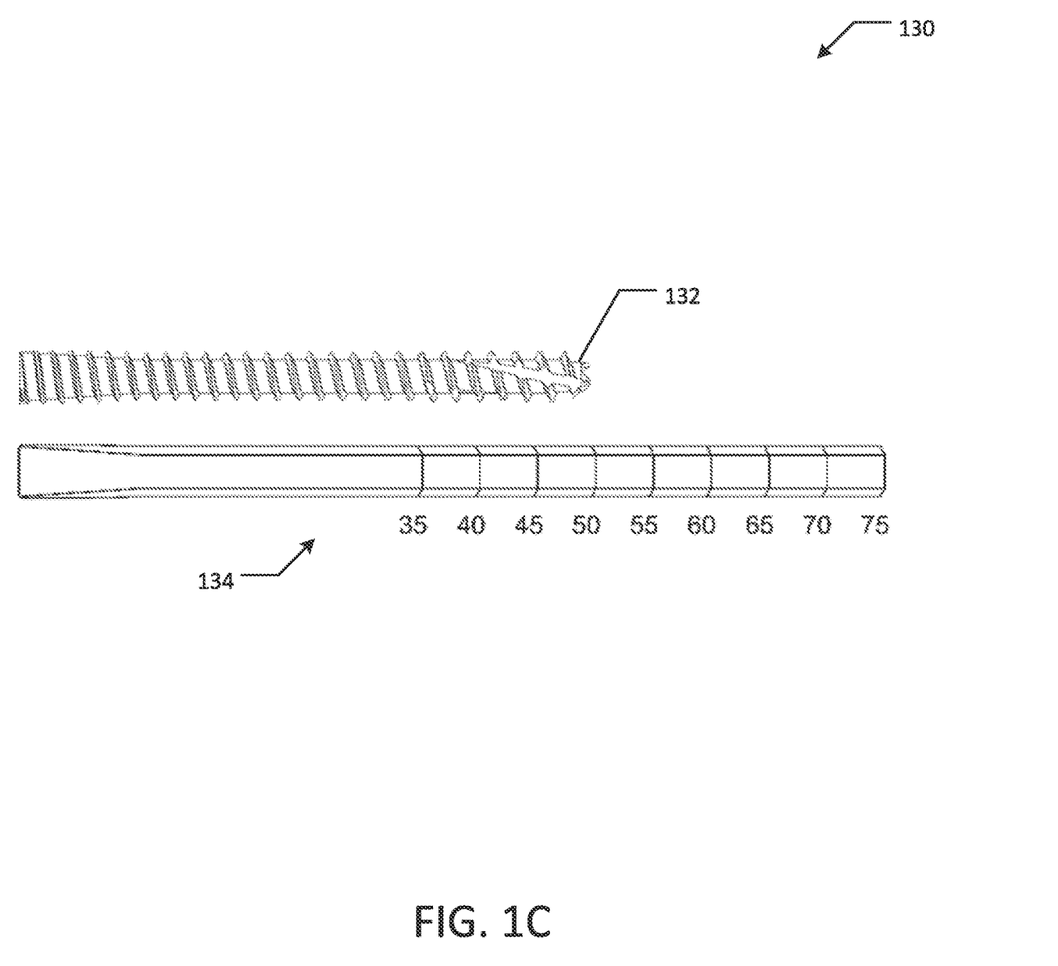
FIG. 1C illustrates an example comparison of an implant screw next to a set of markings, according to an aspect of the present disclosure.

In at least some aspects, the set of markings of the medical device 100 include multiple length markings 110A, 110B indicative of various implant screw lengths. The length markings 110A, as illustrated, may be lines perpendicular to the first diameter markings 106A, 106B. It should be appreciated that only one line is indicated with a reference numeral solely to maintain clarity in the figure. In some instances, the length markings 110A may be evenly distributed. In other instances, the length markings 110A may be unevenly distributed. In at least some aspects, the length markings 110A indicate a length in relation to the distal end 112 of the markings. The length markings 110B, as illustrated, may be numerical indicators corresponding to respective lines of the length markings 110A. The numerical indicators may indicate a length in a unit of measurement (e.g., millimeters). For example, FIG. 1C illustrates an example comparison 130 of an implant screw 132 having a length of fifty millimeters next to a set of markings 134. Lining up one end of the implant screw 132 with the distal end of the markings 134 results in the other end of the implant screw 132 lining up with the "50" length marking. Including the length markings 110B on the medical device 100 enables a medical professional, when analyzing a radiographic image including the set of markings, to quickly determine a length corresponding to a length marking 110A. It also eliminates the need for the medical professional to have to consult materials or information outside of the radiographic image itself. Accordingly, these advantages decrease procedure time and decrease a risk of error.

Figure 2:
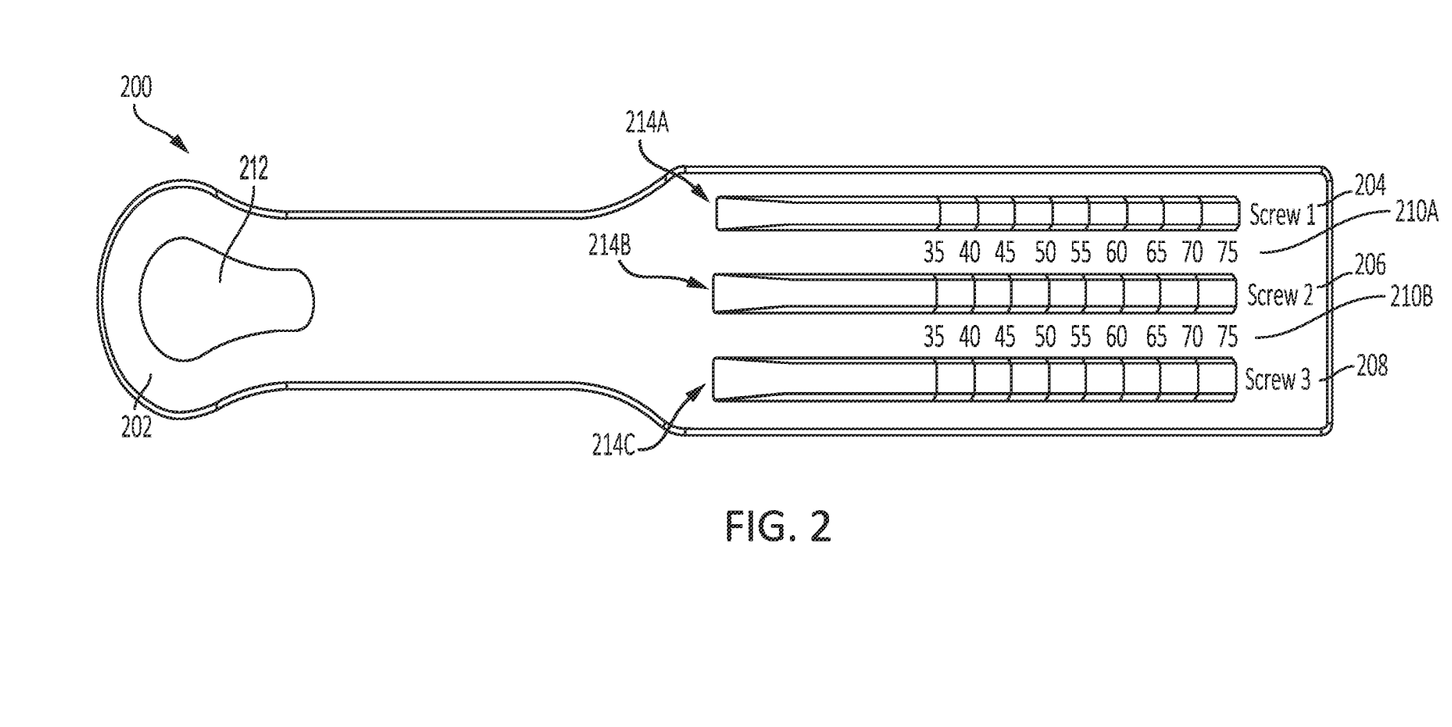
FIG. 2 illustrates an example medical device including multiple sets of markings indicative of different implant screws, according to an aspect of the present disclosure.

FIG. 2 shows an example medical device 200 that includes multiple sets of markings indicative of different implant screws, according to an aspect of the present disclosure. The example medical device 200 includes a body 202. The body 202 includes a radiolucent material such that x-rays pass through the body 202. When the medical device 200 is radiographically imaged, the body 202 therefore fails to appear on the generated radiographic image. For example, the body 202 may be constructed of Polyether ether ketone (PEEK), acetal, ABS, nylon, carbon fiber, polycarbonate, or other suitable materials. In some instances, the body 202 may include an opening 212. The opening 212 may enable easier storage or transportation of the medical device 200, for example, by hanging the medical device 200 on a hook or attaching the medical device 200 to a clip. The opening 212 may also make it easier for a medical professional to hold the medical device 200 using forceps while positioning the device to capture a radiographic image.

The medical device 200 also includes multiple sets of markings 214A, 214B, 214C on the body 202. For example, the medical device 200 may include two, three, four, or any other suitable number of sets of markings. The sets of markings 214A, 214B, 214C include a radiopaque material that prevents x-rays from passing through the markings. When the medical device 200 is radiographically imaged, the sets of markings 214A, 214B, 214C therefore appear on the generated radiographic image. For example, the sets of markings 214A, 214B, 214C may be composed of barium sulfate, bismuth, tungsten, stainless steel, titanium, cobalt chrome, radiopaque inks, or other suitable materials. Each set of markings on the body 202 of the example medical device 200 is indicative of information pertaining to a particular implant screw. For example, the set of markings 214A is indicative of the implant screw corresponding to the screw indicator 204, the set of markings 214B is indicative of the implant screw corresponding to the screw indicator 206, and the set of markings 214C is indicative of the implant screw corresponding to the screw indicator 208.

In some aspects of the present disclosure, each set of markings 214A, 214B, 214C may include the markings as described above in connection with the set of markings of the example medical device 100. For example, the set of markings 214A may include first diameter markings of the implant screw corresponding to the screw indicator 204. The first diameter markings may be indicative of the major diameter of the implant screw. The set of markings 214A may also, in some instances, include second diameter markings of the implant screw corresponding to the screw indicator 204. The second diameter markings may be indicative of the minor diameter of the implant screw. The set of markings 214A may additionally include length markings. The length markings may include line indicators and/or numerical indicators. The set of markings 214A may also include the screw indicator 204 indicative of the implant screw that the set of markings 214A correspond to. The set of markings 214B and the set of markings 214C, in various examples, may include the same markings as the set of markings 214A, but indicative of the implant screws corresponding to the screw indication 206 and the screw indication 208, respectively.

In another example, the set of markings 214 may include first diameter markings indicative of a diameter (e.g., major diameter) of a first implant screw and second diameter markings indicative of a diameter (e.g., major diameter) of a second implant screw. In such an example, the set of markings 214 may also include additional diameter markings, such as major and minor diameter markings for the first implant screw and major and minor diameter markings for the second implant screw. The markings corresponding to the first implant screw may be distinguished from the markings corresponding to the second implant screw. For example, the first implant screw markings may be solid lines while the second implant screw markings may be dashed lines. In this example, the set of markings 214B and the set of markings 214C may include the same described markings as the set of markings 214A, but indicative of different implant screws.

In other aspects, one or more of the sets of markings 214A, 214B, 214C may include less than the markings described above in connection with the set of markings of the example medical device 100. For example, as illustrated in FIG. 2, the set of markings 214A includes numerical length indicators 210A and the set of markings 214B includes numerical length indicators 210B, but the set of markings 214C does not include numerical length markings. This example configuration enables the medical device 200 to be more compact than if the body 202 was expanded to create space for additional numerical length indicators below the set of markings 214C, while still providing the same amount of information. For instance, the numerical length markings 210A may correspond to both the set of markings 214A and the set of markings 214B, and the numerical length markings 210B may correspond to both the set of markings 214B and the set of markings 214C. In other examples, a medical device 200 may be provided with only the numerical length indicators 210A or only the numerical length indicators 210B. For instance, if the line indicators of the length markings are symmetrical among the sets of markings 214A, 214B, 214C, then a single set of numerical length indicators may be sufficient to indicate the corresponding numerical length of the line indicators.

The example medical device 200 may help provide additional information to a medical professional when compared to the example medical device 100 and other typical screw sizing devices. For instance, a medical professional may position the example medical device 200 relative to a patient such that a particular set of markings (e.g., the set of markings 214B) is positioned over the intramedullary canal of interest and may capture a radiographic image. Even though the set of markings 214B was positioned over the intramedullary canal, the generated radiographic image includes all of the sets of markings 214A, 214B, 214C of the example medical device 200. Therefore, the medical professional can reference each of the sets of markings 214A, 214B, 214C directly on the radiographic image when making an implant screw size determination. The medical device 200 may also therefore reduce a patient's x-ray exposure by enabling a medical professional to take less images. Additionally, the example medical device 200 enables a medical professional to use a single tool (or less tools) than if each implant screw had its own respective device (e.g., the medical device 100) with markings indicative of the implant screw. The elimination of separate tools can help with storage and organization in the medical and/or surgical environment.

The example medical device 100 and example medical device 200 may be utilized to determine a proper implant screw size for the intramedullary canals of various bones of patients. For example, the medical device 100 and medical device 200 may include markings indicative of implant screws sized for the intramedullary canals of a patient's metacarpal, phalange, metatarsal, radius, ulna, fibula, carpal, and/or tarsal bones. The respective body 102 and 202 of the medical devices 100 and 200 may be sized accordingly to accommodate markings that are indicative of implant screws sized for the variously sized intramedullary canals.

In some instances, additional modifications may be made to the medical device 100 and/or the medical device 200 as will be apparent to one having skill in the art. For example, the medical device 100 and/or the medical device 200 may include a handle extending from an end of the device to enable a medical professional to hold the device in place when capturing a radiographic image. In some examples, the medical device 100 and/or the medical device 200 may be a single use disposable. In other examples, the medical device 100 and/or the medical device 200 may be a multi-use sterilizable instrument.

An example method of selecting an implant screw size using the provided medical device will now be described. To determine a desired implant screw size using the presently disclosed medical device, a medical professional may position the medical device relative to a damaged bone of the patient. For example, a patient may have fractured a third metacarpal. In such an example, the medical professional may position the medical device relative to the patient's fractured third metacarpal.

Figure 3:
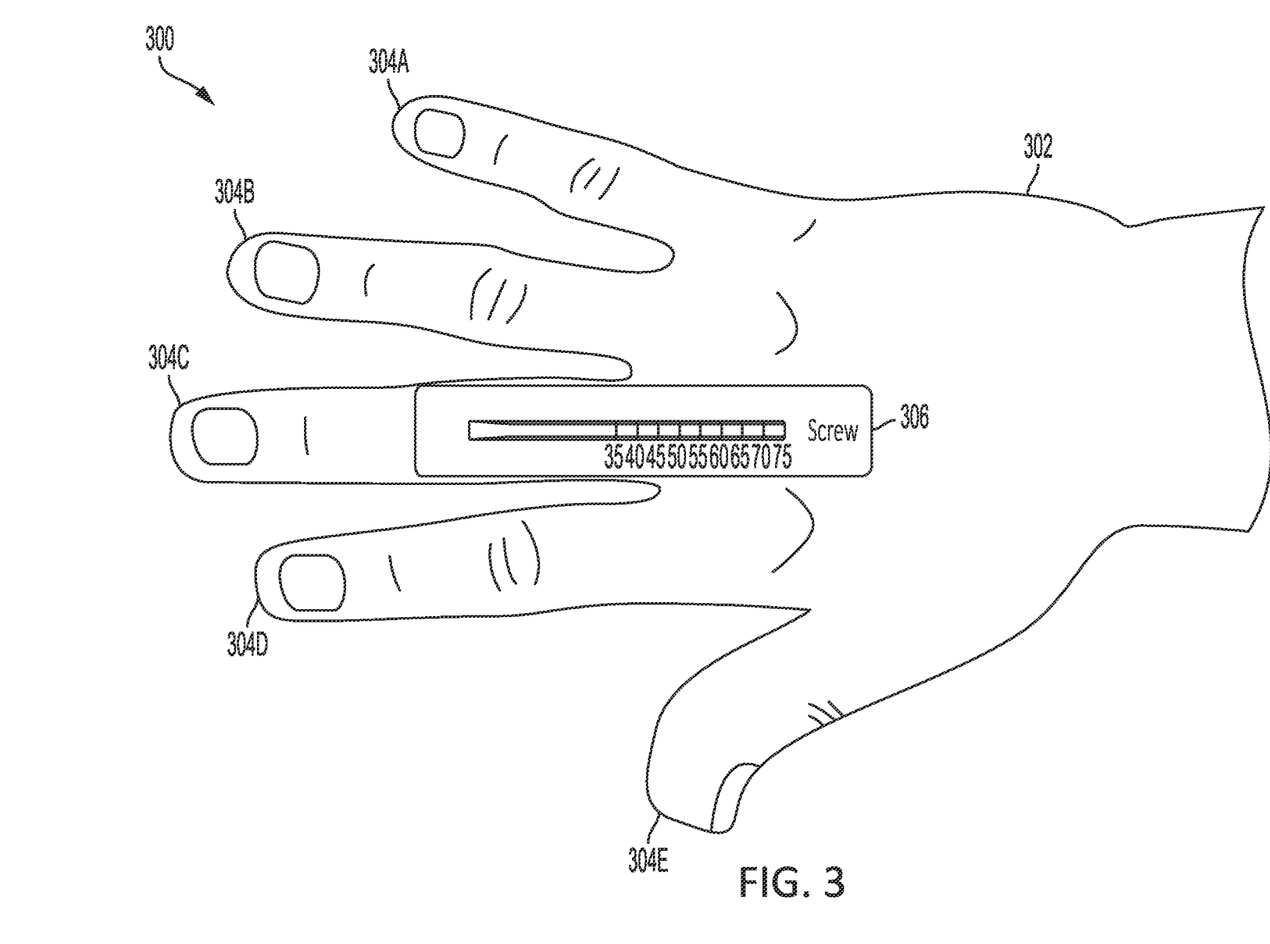
FIG. 3 illustrates an example medical device positioned relative to a patient's damaged metacarpal, according to an aspect of the present disclosure.

FIG. 3 shows an example positioning 300 of an example medical device 306 over the top side of a patient's hand and relative to the patient's third metacarpal. For context, a patient's hand 302 is shown with the patient's five fingers 304A-304E. The example medical device 306 may be configured according to the example medical device 100 described above, in various instances. In other instances, the example medical device 306 may be configured according to the example medical device 200 described above. In the illustrated example, the medical device 306 includes first diameter markings, second diameter markings, line length markings, numerical length markings, and a screw indicator marking. As illustrated, the medical device 306 may be positioned over the patient's hand 302 such that the set of markings (e.g., the diameter markings and length markings) indicative of the implant screw are positioned over the patient's third metacarpal. Stated differently, the medical professional attempts to position as closely as possible the implant screw markings over the intramedullary canal of the patient's third metacarpal.

Once the medical device 306 is positioned, the medical professional may expose an area (e.g., the hand) of the patient to radiation to generate a radiographic image. For example, the medical professional may take an x-ray of the patient's hand 302 with the medical device 306 positioned over the patient's hand as described above. Because the markings of the medical device 306 include a radiopaque material, as described above, a reproduction of the markings appears overlaid on the patient's bone in the generated radiographic image.

Although FIG. 3 illustrates the medical device 306 positioned over the top side of the patient's hand, in other examples, the medical professional may position the medical device over the bottom, or palm, side of the patient's hand. In one example, a medical professional may obtain an x-ray image with the medical device 306 positioned over the top side of the patient's hand and an x-ray image with the medical device 306 positioned over the bottom, or palm, side of the patient's hand. In such an example, the medical professional can average the measurement results obtained from the two x-ray images. Averaging the results in this way can, in some instances, be beneficial to help avoid any issues with magnification of one or both of the x-ray images.

Figure 4:
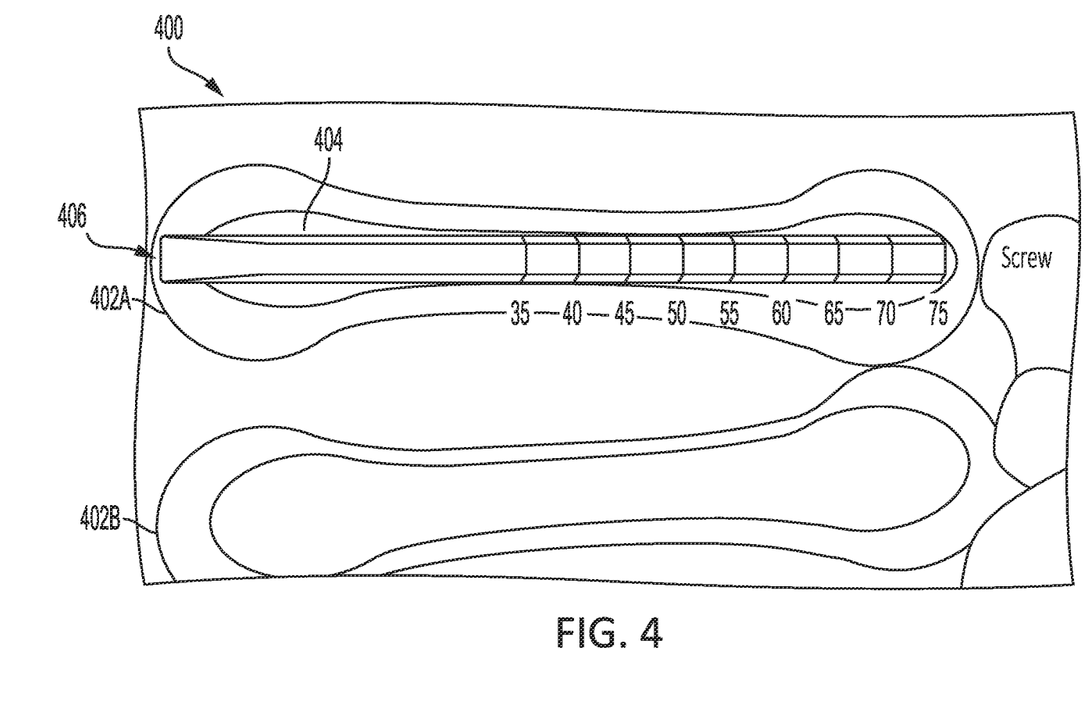
FIG. 4 illustrates an example radiographic image of a patient's hand that includes reproduced markings from an example medical device, according to an aspect of the present disclosure.

FIG. 4 shows an example generated radiographic image 400 that includes reproduced markings overlaid on the patient's bone, according to an aspect of the present disclosure. The radiographic image 400 includes an image of the patient's third metacarpal 402A, including the intramedullary canal 404 of the third metacarpal, and the patient's second metacarpal 402B. The radiographic image 400 also includes a set of markings 406 that are a reproduction of the set of markings on the imaged example medical device 306. Based on the radiographic image 400, the medical professional may determine a desired diameter (e.g., major and/or minor diameter) of the implant screw. The medical professional may also determine a desired length of the implant screw.

For example, the medical professional may compare the reproduction of the first diameter markings (e.g., major diameter markings) to the image of the intramedullary canal 404. This comparison may involve determining whether the first diameter markings are wider than the intramedullary canal 404. If the first diameter markings are wider, then this indicates that the implant screw's threads will engage with the bone (e.g., the third metacarpal 402A). If the first diameter markings are narrower than the intramedullary canal 404, then this indicates that the implant screw's diameter is too narrow because the implant screw's threads will not engage the third metacarpal 402A. If the implant screws threads do not engage the intramedullary canal of the third metacarpal, the implant screw will not fix in place the fractured bone fragments of the third metacarpal. Therefore, first diameter markings being narrower than the intramedullary canal 404 indicate to the medical professional that a larger screw diameter is needed.

The medical professional may also compare the second diameter markings (e.g., minor diameter markings) to the image of the intramedullary canal 404. This comparison may involve determining whether the second diameter markings are wider than the intramedullary canal 404. If the second diameter markings are wider, then this indicates that the implant screw's diameter is too large because the implant screw will not fit within the intramedullary canal 404. If the second diameter markings are narrower than the intramedullary canal 404, then this indicates that the implant screw will fit within the intramedullary canal 404. Therefore, in some instances, a desired diameter of the implant screw may include a first diameter wider than the intramedullary canal 404 and a second diameter narrower than the intramedullary canal 404. Stated differently, in such instances, a desired diameter may include a major diameter large enough that the implant screw's threads will sufficiently engage the bone (e.g., the third metacarpal 402A) and a minor diameter small enough that the implant screw fits within the intramedullary canal 404.

Additionally, the medical professional may compare the length markings to the image of the intramedullary canal 404. This comparison may involve comparing (1) a length from the distal end (e.g., as described above in connection with FIG. 1) of the markings to a line indicator length marking, to (2) the length of the intramedullary canal 404. A desired length of the implant screw may depend on various factors that a medical professional considers. For instance, the medical professional may desire to use as long of an implant screw as possible based on the fracture severity and location.

If after the above-described comparisons the medical professional is unable to determine a desired diameter and/or desired length of the implant screw, the medical professional may capture a second radiographic image. For example, a medical professional may determine that the markings on the radiographic image may be indicative of an undesirable implant screw size, though the medical professional is unsure, based on the radiographic image, of which of the other available implant screw sizes is the desired size. In instances in which the medical professional utilizes an example medical device 100 including a single set of markings, the medical professional may position a second medical device 100 relative to the patient's bone and again expose the area of the patient with the bone and the second medical device 100 to generate a radiographic image. The second medical device 100 includes a set of markings indicative of an implant screw that has a different size (e.g., different diameter) than the implant screw indicated by the markings on the initial medical device 100. The medical professional may then conduct the comparisons described above on the second radiographic image to determine a desired diameter and length of the implant screw.

In other instances in which the medical professional utilizes an example medical device 200 including multiple sets of markings, the medical professional may reposition the same medical device 200 such that a second set of markings, different than the first set, is positioned over the patient's bone. The medical professional may then again expose the area of the patient with the bone and the medical device 200 to generate a radiographic image. The second set of markings includes a set of markings indicative of an implant screw that has a different size (e.g., different diameter) than the implant screw indicated by the first set of markings. The medical professional may then conduct the comparisons described above on the second radiographic image to determine a desired diameter and length of the implant screw. The medical professional may repeat the image capturing process as many times as needed, while keeping in mind patient radiation levels, to determine a desired diameter and length of the implant screw. The medical professional may also alternatively capture multiple radiographic images of different sets of markings before determining a desired implant screw sizing, rather than capturing additional images after being unable to determine a desired sizing.

The above-described method provides a medical professional with more information than typical implant screw sizing devices. For example, the method may provide a medical professional with information on the major and minor diameter of an implant screw and the various implant screw lengths, all overlaid on an image of a patient's intramedullary canal. The method may also provide a medical professional with information on multiple implant screw diameters on the same radiographic image. Accordingly, the method may help a medical professional quickly and easily determine a proper implant screw diameter and length in a non-invasive manner either prior to the start of surgery or intraoperatively. For instance, a radiographic image that includes the markings of the provided medical device overlaid on a patient's intramedullary canal may help a medical professional quickly and easily determine how the implant screw will engage the patient's bone prior to the medical professional drilling or inserting the implant screw.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated.

The invention is claimed as follows:

1. A medical device comprising:
   a base component constructed of a radiolucent material; and
   a set of markings on the base component, the set of markings including: (i) first diameter markings indicative of a first diameter of an implant screw, (ii) second diameter markings indicative of a second diameter of the implant screw, wherein the second diameter markings are between the first diameter markings on the base component, and (iii) a plurality of length markings indicative of a plurality of length options of the implant screw,
   wherein the set of markings are composed of a radiopaque material.

2. The medical device of claim 1, wherein the first diameter of the implant screw corresponds to a major diameter of a thread of the implant screw.

3. The medical device of claim 1, wherein the second diameter of the implant screw corresponds to a minor diameter of a thread of the implant screw.

4. The medical device of claim 1, wherein the implant screw that the set of markings are indicative of is adapted to be placed within an intramedullary canal of at least one of a metacarpal, phalange, metatarsal, radius, ulna, fibula, carpal, or tarsal bone of a patient.

5. The medical device of claim 1, wherein the implant screw that the set of markings are indicative of is adapted to be placed within an intramedullary canal of a radius bone of a patient.

6. The medical device of claim 1, wherein the radiolucent material is at least one of the materials selected from the group consisting of Polyether ether ketone (PEEK), acetal, ABS, nylon, carbon fiber, and polycarbonate.

7. The medical device of claim 1, wherein the radiopaque material is at least one of the materials selected from the group consisting of barium sulfate, bismuth, tungsten, stainless steel, titanium, cobalt chrome, and radiopaque inks.

8. The medical device of claim 1, further comprising a screw indicator that indicates at least one of a diameter, a type, and a model of the implant screw.

9. The medical device of claim 1, wherein the second diameter markings are indicative of a diameter of a second implant screw.

10. The medical device of claim 1, further comprising the implant screw.

11. A medical device comprising:
    a base component constructed of a radiolucent material; and
    a plurality of sets of markings on the base component, wherein each set of markings is indicative of a respective implant screw of a plurality of implant screws,
    wherein each set of markings includes:
      first diameter markings indicative of a first diameter of the respective implant screw;
      second diameter markings indicative of a second diameter of the respective implant screw, wherein the second diameter markings are between the first diameter markings on the base component; and
      a plurality of length markings indicative of a plurality of length options of the respective implant screw, and
    wherein the plurality of sets of markings are composed of a radiopaque material.

12. The medical device of claim 11, wherein each implant screw of the plurality of implant screws that the plurality of sets of markings are indicative of is adapted to be placed within an intramedullary canal of at least one of a metacarpal, phalange, metatarsal, radius, ulna, fibula, carpal, or tarsal bone of a patient.

13. The medical device of claim 11, wherein each implant screw of the plurality of implant screws that the plurality of sets of markings are indicative of is adapted to be placed within an intramedullary canal of a radius bone of a patient.

14. The medical device of claim 11, wherein the plurality of sets of markings includes two or three sets of markings.

15. The medical device of claim 11, further comprising screw indicators that indicate at least one of a diameter, a type, and a model of the implant screws.

16. The medical device of claim 11, further comprising the implant screws.

17. The medical device of claim 11, wherein the first diameter markings of each of the plurality of sets of markings has a width, and the widths of the first diameter markings of the plurality of sets of markings are different among each other.

18. The medical device of claim 11, wherein the second diameter markings of each of the plurality of sets of markings has a width, and the widths of the second diameter markings of the plurality of sets of markings are different among each other.

19. The medical device of claim 11, further comprising one or more length indicators.

20. The medical device of claim 19, wherein the one or more length indicators are disposed between two adjacent sets of markings among the plurality of sets of markings.

* * * * *